United States Patent [19]
McHughen et al.

[11] Patent Number: 5,973,227
[45] Date of Patent: Oct. 26, 1999

[54] FLAX TRANSFORMATION

[75] Inventors: Alan McHughen, Corman Park; Teguh Wijayanto, Saskatoon, both of Canada

[73] Assignee: University of Saskatchewan, Saskatoon, Canada

[21] Appl. No.: 09/073,904

[22] Filed: May 6, 1998

[51] Int. Cl.⁶ .............. C12N 15/82; C12N 5/04; A01H 5/00; A01H 4/00
[52] U.S. Cl. .......... 800/293; 800/298; 435/470; 435/419; 435/430.1; 435/431
[58] Field of Search ................ 435/468, 470, 435/419, 420, 430.1, 431; 800/278, 293, 298

[56] References Cited

U.S. PATENT DOCUMENTS

| | | | |
|---|---|---|---|
| 4,945,050 | 7/1990 | Sanford et al. | 435/470 |
| 5,015,580 | 5/1991 | Christou et al. | 435/470 |
| 5,036,006 | 7/1991 | Sanford et al. | 435/470 |
| 5,179,022 | 1/1993 | Sanford et al. | 435/470 |
| 5,204,253 | 4/1993 | Sanford et al. | 435/468 |
| 5,324,646 | 6/1994 | Buising et al. | 435/468 |
| 5,484,956 | 1/1996 | Lundquist et al. | 435/468 |
| 5,489,520 | 2/1996 | Adams et al. | 435/468 |
| 5,508,468 | 4/1996 | Lundquist et al. | 800/278 |
| 5,538,877 | 7/1996 | Lundquist et al. | 435/468 |
| 5,538,880 | 7/1996 | Lundquist et al. | 435/468 |
| 5,610,042 | 3/1997 | Chang et al. | 435/468 |

OTHER PUBLICATIONS

Dong & McHughen, "Transgenic flax plants from Agrobacterium mediated transformation: incidence of chimeric regenerants and inheritance of transgenic plants," *Plant Science*, (1993), vol. 91, pp. 139–148.

Jordan & McHughen, "Glyphosate tolerant flax plants from Agrobacterium mediated gene transfer," *Plant Cell Reports*, (1988) vol. 7, pp. 281–284.

Dong & McHughen, "An improved procedure for production of transgenic flax plants using *Agrobacterium tumefaciens*, "*Plant Science*, (1993) vol. 88, pp. 61–71.

McHughen, "Agrobacterium mediated transfer of chlorsulfuron resistance to commercial flax cultivars," *Plant Cell Reports*, (1989) vol. 8, pp. 445–449.

Dong & McHughen, "Patters of transformation intensity on flax hypocotyls inoculated with *Agrobacterium tumefaciens*," *Plant Cell Reports*, (1991) vol. 10, pp. 555–560.

Dong et al, Plant Science, vol. 88, pp. 61–71, 1993.
Sanford et al, Meth. Enzymol., vol. 217, pp. 483–509, 1993.
Seki et al, Plant Mol. Biol., vol. 17, pp. 259–263, 1991.
Christou, Meth. Cell Biol., vol. 50, pp. 375–382, 1995.

*Primary Examiner*—David T. Fox
*Assistant Examiner*—Ashwin D. Mehta
*Attorney, Agent, or Firm*—Klarquist, Sparkman, Campbell, Leigh & Whinston, LLP

[57] ABSTRACT

Improved compositions and methods for transformation of flax by microprojectile bombardment and regeneration of fertile transgenic flax plants are provided.

5 Claims, No Drawings

FLAX TRANSFORMATION

BACKGROUND OF THE INVENTION

This invention relates to compositions and methods related to the genetic transformation of flax.

The ability to genetically engineer flax (*Linum usitatissimum* L.) to improve its performance and stress-resistance or to enhance alternative uses is of great importance.

Genetic transformation and recovery of fertile flax plants using Agrobacterium have been reported previously (Jordan and McHughen, *Plant Cell Rep.* 7:281–284, 1988). However, transformation of flax using Agrobacterium has serious limitations, including low transformation efficiency, a high incidence of somaclonal variation resulting from in vitro culture of callus tissue, a high incidence of chimeric regenerants (Dong and McHughen, *Plant Sci.* 88:61–71, 1993a; Dong and McHughen, *Plant Sci.* 91:139–148, 1993b), and a high incidence of escape shoots, i.e., shoots arising from non-transformed cells protected from selection by transformed cells (McHughen and Jordan, *Plant Cell. Rep.* 7:611–614, 1989).

SUMMARY OF THE INVENTION

We have developed improved methods for transformation and regeneration of flax using particle bombardment.

One aspect of the present invention encompasses methods for producing a transgenic flax plant that includes the steps of preculturing a flax cell on a regeneration induction medium; bombarding the precultured flax cell with a microprojectile that is coated with or otherwise comprises a nucleic acid, thereby producing a transformed flax cell that comprises the nucleic acid; and regenerating a transgenic flax plant from the transformed flax cell. In one embodiment, the flax cell (e.g., flax hypocotyl tissue) is precultured for at least two days prior to bombardment. According to another embodiment, the precultured flax cell is bombarded at an acceleration pressure of 650 psi to 900 psi. A preferred target tissue for microprojectile bombardment is hypocotyl tissue. According to another embodiment, the regeneration induction medium comprises a carbohydrate, a cytokinin (e.g., 6-benzylaminopurine) and an auxin (e.g., 1-naphthaleneacetic acid). One such regeneration induction medium is MS-1 medium.

The foregoing and other aspects of the invention will become more apparent from the following detailed description.

DETAILED DESCRIPTION OF THE PREFERRED EMBODIMENTS

We have developed methods for flax transformation using microprojectile bombardment and high-efficiency regeneration of fertile transgenic flax.

Definitions and Methods

Unless otherwise noted, terms are to be understood according to conventional usage by those of ordinary skill in the relevant art. In addition to the definitions of terms provided below, definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994.

Particle Bombardment

Microprojectile bombardment is a method of gene transfer that uses high velocity DNA-coated particles, or microprojectiles, that are propelled at high velocity and penetrate target cells, thereby delivering the DNA into the interior of the target cells where the DNA is transiently and/or stably expressed.

Plant Transformation and Regeneration

"Cell": The term "cell" as used to refer to a target for microprojectile bombardment includes single, isolated cells and cells that are part of a tissue, organ, or whole organism that is such a target.

"Transformed": "Transgenic". A cell (or tissue, organ, or organism) into which an exogenous nucleic acid (i.e., a "transgene") has been introduced is considered "transformed" or "transgenic," as is the progeny of the cell in which the introduced nucleic acid is present.

A transgene includes nucleic acid sequences that are foreign to the host cell. Alternatively, the transgene includes a nucleic acid sequence that was derived from the genome of the host cell but has been modified in some way (e.g., mutated or placed under the control of a promoter, terminator, etc., with which the sequence is not normally associated) or has been integrated into the host cell genome at a location that is different than its normal location in the host cell genome.

Transformation by Particle Bombardment. Successful transformation by particle bombardment requires that the target cells are actively dividing, accessible to microprojectiles, culturable in vitro, and totipotent, i.e., capable of regeneration to produce mature plants, preferably fertile plants.

The target tissue for microprojectile bombardment of flax is preferably epidermal tissue, including but not limited to, epidermal cells of hypocotyls excised from flax seedlings. Alternative target tissues include, but are not limited to, stem, leaf, and cotyledon tissue.

In Vitro Culture and Regeneration of Transformed Flax Cells: "Transformation Efficiency": "Plant Culture Medium". We have found that preculturing flax tissue prior to microprojectile bombardment improves the efficiency of transformation. "Transformation efficiency" refers to the increase in the number of target cells expressing GUS activity (transiently) concomitant with an increase in preculture period.

As used herein, "plant culture medium" refers to any medium used in the art for supporting viability and growth of flax tissue, including cultured cells and excised plant parts, or for growth of whole plant specimens. Such media can include: macronutrients such as nutritional sources of nitrogen, phosphorus, potassium, sulfur, calcium, magnesium, and iron; micronutrients such as nutritional sources of boron, molybdenum, manganese, cobalt, zinc, copper, chlorine, and iodine; carbohydrates (e.g., sucrose, maltose, and saccharose, for example at about 3% to about 6%); vitamins; phytohormones; selection agents (for transformed cells or tissues, e.g., antibiotics or herbicides); and gelling agents (e.g., agar, Bactoagar, agarose, Phytagel™, Gelrite™, etc.); and may include undefined components, including, but not limited to: coconut milk, casein hydrolysate, yeast extract, and activated charcoal.

In the Example below, flax hypocotyl tissue was precultured on a regeneration induction medium, MS-1, that included a carbohydrate (3% sucrose), a cytokinin [1.0 mg/L 6-benzylaminopurine (BA)] and an auxin [0.02 mg/L 1-naphthaleneacetic acid (NAA)]. However, any medium conventionally used for flax cell culture and transformation can be used with the transformation methods disclosed herein. In fact, flax regeneration has been noted on basal medium (such as Murashige and Skoog medium ["MS"; Murashige and Skoog, *Physiol. Plant.* 15:473, 1962)]) alone without added phytohormones. Media that are useful for flax regeneration in vitro (i.e., "regeneration induction media") include, but are not limited to: MS medium supplemented with 6-benzylaminopurine (BA) (Lane, *Physiol. Plant.* 45:260–264, 1979; MS supplemented with kinetin and indole-3-butyric acid (IBA) (McHughen and Swartz, *J. Plant Physiol.* 117:109–117, 1984); MS supplemented with zeatin and indole-3-acetic acid (IAA) (Millam et al., *Plant Cell Tiss. Org. Cult.* 28:163–166, 1992); MS supplemented with TDZ and naphthaleneacetic acid (NAA) (Bretagne et al., *Plant Cell Reports* 14:120–124, 1994); and Linsmaier and Skoog medium ("LS"; Linsmaier and Skoog, *Physiol. Plant.* 18:100, 1965) supplemented with kinetin and NAA (Rybczynski, *Genet. Pol.* 16:1–12, 1975).

After microprojectile bombardment, transformed plant tissue is further cultured on a regeneration induction medium to cause differentiation of the tissue to produce a transgenic plant.

Any well-known auxin or cytokinin may be used in the practice of the invention. Auxins include, but are not limited to, NAA, IAA, IBA, etc. Cytokinins include, but are not limited to, BA, kinetin, and zeatin, etc.

"Plant". The term "plant" encompasses transformed plants, progeny of such transformed plants, and parts of plants, including seeds, fiber, cultured cells, etc.

Nucleic Acids

"Isolated". An "isolated" nucleic acid is a nucleic acid that has been substantially separated or purified away from other nucleic acid sequences in the cell of the organism in which the nucleic acid naturally occurs, i.e., other chromosomal and extrachromosomal DNA and RNA. The term also embraces recombinant nucleic acids and chemically synthesized nucleic acids.

"Operably Linked". A first nucleic-acid sequence is "operably" linked with a second nucleic-acid sequence when the first sequence affects the function of the second sequence, as when a promoter element causes or modulates the transcription of a protein-coding sequence, or when two protein-coding sequences are joined so as to be contiguous and in the same reading frame, thereby resulting in production of a fusion polypeptide that includes functional features of the two sequences.

"Recombinant". A "recombinant" nucleic acid is made by an artificial combination of two otherwise separated nucleic-acid segments, e.g., by chemical synthesis or by conventional recombinant DNA techniques.

Vectors, Transformation, Host cells. Nucleic acids can be cloned or otherwise incorporated into nucleic-acid constructs or vectors for introduction into and replication and/or transcription in a host cell.

For the practice of the present invention, conventional compositions and methods for preparing and using vectors and host cells are employed, as discussed, inter alia, in Sambrook et al., *Molecular Cloning: A Laboratory Manual*, 2nd ed., vol. 1–3, Cold Spring Harbor Laboratory Press: Cold Spring Harbor, New York, 1989, or Ausubel et al., *Current Protocols in Molecular Biology*, Greene Publishing and Wiley-Interscience, New York, 1992 (with periodic updates).

A number of vectors suitable for stable transformation of plant cells or for the establishment of transgenic plants have been described, for example, in: Pouwels et al., *Cloning Vectors: A Laboratory Manual*, 1985, supp. 1987; Weissbach and Weissbach, *Methods for Plant Molecular Biology*, Academic Press, New York, 1989; and Gelvin et al., *Plant Molecular Biology Manual*, Kluwer Academic Publishers, 1990. One or more cloned plant genes can be operably linked with, for example, a promoter, transcription initiation start site, ribosome binding site, RNA processing signal, polyadenylation signal, intron(s), and transcription termination signal (e.g., the potato PI-II terminator or the octopine or nopaline synthase 3' terminators).

Examples of constitutive plant promoters useful for expressing genes in plant cells include, but are not limited to, the cauliflower mosaic virus (CaMV) 35S promoter, maize ubiquitin (Ubi-1) promoter, rice actin (Act) promoter, nopaline synthase promoter, and the octopine synthase promoter. A variety of plant gene promoters that are regulated in response to environmental, hormonal, chemical, and/or developmental signals also can be used for expression of foreign genes in plant cells, including promoters regulated by heat (e.g., heat shock promoters); light (e.g., pea rbcS-3A or maize rbcS promoters or chlorophyll a/b-binding protein promoter); phytohormones, such as abscisic acid; wounding (e.g., wunI); anaerobiosis (e.g., Adh); and chemicals such as methyl jasmonate, salicylic acid, or safeners. Well known cell-, tissue-, organ-, developmental stage-specific promoters also can be used.

Such vectors also can include one or more well known dominant selectable marker genes, including genes encoding antibiotic resistance (e.g., resistance to hygromycin, kanamycin, bleomycin, G418, streptomycin, paromomycin, or spectinomycin) and herbicide-resistance genes (e.g., resistance to phosphinothricin or glyphosate) to facilitate manipulation in bacterial systems and to select for transformed plant cells. Well known screenable marker or reporter genes can also be used, including color markers such as genes encoding β-glucuronidase (GUS) or anthocyanin production, or fluorescent markers such as genes encoding luciferase or green fluorescent protein (GFP).

The invention will be better understood by reference to the following Example, which is intended merely to illustrate the best mode now known for practicing the invention. The scope of the invention is not to be considered limited thereto.

EXAMPLE

Transformation of Flax by Particle Bombardment and Regeneration of Transgenic Flax We have demonstrated that particle bombardment can deliver foreign DNA into flax cells as determined by reporter gene (GUS) assays and the recovery of mature kanamycin-resistant transformants. Intact hypocotyls of *L. usitatissimum* cv. Somme produced detectable levels of GUS activity after bombardment of tissue with microprojectiles coated with plasmid DNA containing the GUS gene, as determined by the appearance of blue cells following incubation of the bombarded tissue with substrate for the GUS enzyme.

Flax seeds (*L. usitatissimum* cv. Somme) were surface sterilized by soaking in approximately 70% ethanol solution for two minutes, immersed twice in 25% commercial bleach (5.25% sodium hypochlorite) for 12 minutes with continuous stirring, then washed three times with sterile double-distilled water. The seeds were then drained on sterile filter paper in a laminar flow cabinet to remove excess water. Sterilized seeds (15–20 seeds per plate) were then germinated on MS basal medium with 3% sucrose, 0.8% agar ("MSO") in the dark. Hypocotyl segments (5–7 mm) of 6- to 7-day-old flax seedlings were dissected using sterile scalpels and cultured in regeneration induction medium consisting of 3% sucrose, 0.8% agar, with 1.0 mg/L BA and 0.02 mg/L NAA ("MS1"). For bombardment, 20–30 hypocotyls were arranged in the center of MS1 plates. The plates were maintained in a light bench at 22–24° C., 16 h photoperiod, and light intensity of about 50 $\mu$mol/m$^2$/s for about four days (preculture period) prior to bombardment. All media were adjusted to pH 5.8 prior to autoclaving.

DNA for microprojectile bombardment was purified from p35SGUSINT (Vancanneyt et al., *Mol. Gen. Genet.* 220:245–250, 1990), containing the β-glucuronidase (GUS) and neomycin phosphotransferase (NPTII) genes, introduced into *E. coli* strain DH5α. The intron-containing GUS gene (driven by a CaMV 35S promoter) was used as a reporter gene in the histochemical assay, and the NPTII gene (driven by the NOS promoter), which provides kanamycin resistance was used as a selectable marker (Jefferson et al., *EMBO J.* 6:3901–3907, 1987). Bacteria cultures were prepared by inoculating 1 L liquid LB medium (1% tryptone, 0.5% yeast extract, and 0.5% sodium chloride) containing 50 mg/L kanamycin with 5–10 mL of an overnight bacterial culture in LB medium inoculated with a single colony from a freshly streaked LB plate (LB medium supplemented with agar) containing 50 mg/L kanamycin. The pH of the LB medium was adjusted to 7.0 prior to autoclaving. The bacterial culture was incubated at 37° C. overnight with vigorous agitation until the absorbance at 600 nm (using a spectrophotometer) was about 1.5. Plasmid DNA was purified from the bacterial cells using the Wizard Maxipreps™ kit (Promega). The resulting DNA pellet was resuspended in TE buffer (10 mM Tris-HCl, 1 mM EDTA, pH 8.0). The DNA concentration was quantified using an ultraviolet spectrophotometer (GeneQuant II RNA/DNA calculator, Pharmacia Biotech) at 260 nm and 280 nm and then adjusted to 1.0 μg/μL for bombardment experiments.

Plasmid DNA was precipitated onto gold particles (1.0 μm) by $CaCl_2$-spermidine precipitation (Klein et al., Bio/Tech. 6:559–563, 1988). Plasmid DNA (7.5 μL at 1 μg/μL) was added to 50 μL aliquots of sterilized gold particle suspension. $CaCl_2$ (50 μL, 2.5 M) and 20 μL spermidine solution (0.1 M) were then added to the suspension. After a series of several centrifugations, the final DNA-gold particle suspension was resuspended in 70 L of 100% ethanol (enough for six bombardments). Ten μL of the DNA-coated gold suspension was pipetted and spread onto the center of each macrocarrier. To dry the suspension, the loaded macrocarriers were placed inside a container with drying material (Dryrite™ (anhydrous calcium sulfate, W. A. Hammond Drierite Col, Xenia, Ohio) for about 30 min before bombardment.

Precultured or non-precultured hypocotyls on MS1 media were bombarded once with DNA-coated gold particles using the PDS 1000/He delivery system (Biorad). Several factors affecting transient GUS gene expression were evaluated. Bombardments were performed at various pressures (650 to 1500 psi), hypocotyl preculture periods (0 to 5 days), bombardment distances (represented by the position of macrocarrier stage and sample stage on the slots in the gun chamber). Bombardments were conducted under at least 26 inches Hg chamber vacuum.

After bombardment, the petri plates were sealed and placed in a light bench, as done for preculture, for four days post-bombardment, before being transferred to selection medium and sampled for transient GUS gene expression. To assay for transient GUS gene expression, four bombarded hypocotyl samples were randomly chosen from each plate and immersed in 100–200 μL of X-Gluc (5-bromo-4-chloro-3-indolyl-β-δ-glucuronic acid) solution consisting of 100 mM sodium phosphate (pH 7.0), 0.5 mM potassium ferrocyanide, 0.5 mM potassium ferricyanide, 10 mM ethylene diamine tetraacetic acid (EDTA) and 0.1% X-Gluc in a microtiter plate. X-Gluc is a synthetic substrate for GUS that forms a blue precipitate within transformed cells in which GUS activity is present. The microtiter plate was incubated at 37° C. for 24–48 hr. Assayed hypocotyls were then removed from X-Gluc solution, washed with 95% ethanol, 70% ethanol, and then distilled water. The number of blue spots per hypocotyl was observed under a dissecting microscope, counted, and averaged from these four samples.

Bombarded hypocotyls were cultured on regeneration induction medium (MS1) containing kanamycin (100 or 200 mg/L) to select for transformed cells and maintained in the light bench. Regenerating shoots were recovered when they were approximately 1 cm tall. A basal stem disc (1–2 mm in length) of each resulting shoot was excised for histochemical GUS assay. Shoots from GUS-positive segments were placed on MS5 rooting medium in vials (half-strength MS salts, 3% sucrose, 0.8% agar, pH 5.8, supplemented with 0.1 μM indoleacetic acid, IAA) with or without kanamycin selection (50 or 100 mg/L kanamycin) for rooting. The shoot vials were again maintained in the light bench. Plantlets with positive staining tissues and well developed roots were transplanted into soil in pots in a growth chamber.

The selected plants were allowed to mature, flower, self-pollinate, and set seed. Seed were then germinated and analyzed for meiotic stability and segregation pattern of the transgenes.

The majority of such regenerant plants typically grew and developed in a normal manner. In one experiment, a total of 18 independent transgenic shoots (out of 34 that were subjected to kanamycin selection) were recovered successfully from selection medium. Ten of these 18 shoots grew well, produced roots, and were transferred to soil in a growth chamber. Nine transgenic lines have successfully produced seeds; one of these nine lines showed reduced fertility.

Several factors that might affect the efficiency of transformation were tested. A major factor was the period of preculture of the flax hypocotyls prior to bombardment (Table 1). In general, the number of blue spots (indicating transient cellular GUS expression) increased as the preculture period increased. Only those hypocotyls given a preculture period prior to bombardment gave rise to solid (i.e., nonchimeric) transgenic regenerants. The only regenerant recovered from a non-precultured hypocotyl was chimeric, composed of some transgenic and some non-transgenic cells. Our results indicate that flax transformation via microprojectile bombardment reduces the incidence of chimeras relative to transformation via Agrobacterium. During the preculture period, cells appear to become competent to regenerate into shoots and to initiate cell divisions.

TABLE 1

Number of Blue Spots Per Flax Hypocotyl in Preculture Experiments

| Hypocotyl Preculture (days) | Number of Blue Spots per Hypocotyl (mean + SE)* |
|---|---|
| 0 | 1.04 ± 1.10$^a$ |
| 1 | 1.17 ± 0.54$^a$ |
| 2 | 2.46 ± 1.80$^{ab}$ |
| 3 | 4.21 ± 1.92$^b$ |
| 4 | 8.54 ± 3.34$^c$ |
| 5 | 12.63 ± 9.55$^c$ |

*Average of 6 replicates. Values with same letters (in superscript) are not significantly different (T-test; p <0.05).

Nine of the transgenic lines were produced using relatively low bombardment acceleration pressure (i.e., 650–900 psi); only one had a relatively high acceleration pressure (1550 psi). A possible reason for this result is that the preferred target tissue in the hypocotyl is epidermal tissue, and higher pressure may cause most microprojectiles to penetrate too deeply into the plant tissue, beyond the epidermis. In addition, higher pressure likely causes increased collateral damage to epidermal cells, reducing their capacity to regenerate.

We have found that particle bombardment produces only about one chimera out of ten transformant lines (Table 2), a significant improvement over Agrobacterium-mediated transformation, which produces chimeras in about 45% of transgenic regenerants.

After bombardment, surviving shoots were confirmed for GUS gene expression by assaying stem disc sections with X-Gluc solution. Various levels of GUS gene expression were observed in these shoots, ranging from weak to strong blue staining. The use of kanamycin as a selective agent has proven to be satisfactory for flax bombarded with the NPT-II gene, but other selectable marker genes and selective agents may be used instead.

Eighteen regenerating shoots were excised from bombarded hypocotyls. Of these, ten produced well-developed roots in rooting medium containing 50 mg/L kanamycin, indicating a selection efficiency of over 55%, which is substantially superior to the selection efficiency of only 20% obtained by inoculating hypocotyls with Agrobacterium using the same marker gene and selection agent, kanamycin (Dong and McHughen, *Plant Sci.* 91:139–148, 1993b).

The status of the regenerants as transgenic has been confirmed by progeny segregation ratios (based on GUS histochemical assays), as shown in Table 3. The results of the chi-square analysis indicate that all transformants except #7 have a single Mendelian insert, and that transformant #7 has multiple Mendelian inserts. Of the ten transformant lines, only one was chimeric (#6) and only one was sterile (#3).

TABLE 3

Progeny Segregation Ratios

| Transformant | Chi-Square Analysis | Seeds Tested (GUS$^+$:GUS$^-$) |
|---|---|---|
| 1 | 3:1 | 44:20 |
| 2 | 3:1 | 39:16 |
| 3 | sterile | — |
| 4 | 3:1 | 29:6 |
| 5 | 3:1 | 82:24 |
| 6 | chimera | 2:64 |
| 7 | 15:1 | 92:9 |
| 8 | 3:1 | 39:19 |
| 9 | 3:1 | 8:2 |
| 10 | 3:1 | 15:6 |

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

TABLE 2

Conditions that Produced GUS-Positive Shoots

| Independent Transformant | GUS+ Shoot[1] | Pressure (psi) | Hypocotyl Preculture (days) | Distance[2] | Kanamycin (mg/L) | Recovery Period (Weeks)[3] | Progeny Segregation[4] | Ratio[5] |
|---|---|---|---|---|---|---|---|---|
| 1 | Solid | 900 | 4 | 1–3 | 200 | 16 | 44:20 | 3:1 |
| 2 | Solid | 900 | 4 | 1–3 | 200 | 17 | 39:16 | 3:1 |
| 3 | Solid | 900 | 4 | 1–3 | 100 | 8 | — | — |
| 4 | Solid | 650 | 8 | 1–3 | 200 | 16 | 29:6 | 3:1 |
| 5 | Solid | 900 | 4 | 1–3 | 100 | 5 | 82:24 | 3:1 |
| 6 | Chimera | 900 | 2 | 1–3 | 100 | 5 | 2:64 | — |
| 7 | Solid | 900 | 4 | 1–4 | 100 | 8 | 92:9 | 15:1 |
| 8 | Solid | 1550 | 4 | 1–3 | 100 | 5 | 39:19 | 3:1 |
| 9 | Solid | 900 | 4 | 1–4 | 100 | 7 | 8:2 | 3:1 |
| 10 | Solid | 900 | 4 | 1–3 | 100 | 7 | 15:6 | 3:1 |

[1] Based on stem-section GUS assays of independent transformants.
[2] Represents the position of macrocarrier and sample stages, respectively, in the gun chamber slots.
[3] Approximate period from transferring hypocotyls on selection media to recovering positive transformants.
[4] GUS assay on germinated seedlings; #GUS$^+$ seedlings: #GUS seedlings.
[5] Predicted ratio based on $\chi^2$ analysis.

What is claimed is:

1. A method for producing a transgenic flax plant, comprising:
    preculturing a flax hypocotyl tissue comprising epidermal tissue on a regeneration induction medium;
    bombarding the precultured flax hypocotyl tissue with a microprojectile that comprises a nucleic acid, thereby producing a transformed flax hypocotyl comprising transformed flax cells that comprise the nucleic acid; and
    regenerating a transgenic flax plant from the transformed flax hypocotyl tissue.

2. The method of claim 1 wherein the hypocotyl is precultured for about 4 days.

3. The method of claim 1 further comprising bombarding the flax hypocotyl in a vacuum chamber having a chamber vacuum pressure of at least 26 inches Hg.

4. The method of producing a transgenic flax plant according to claim 1 wherein bombarding the hypocotyl is performed with an acceleration pressure of between 650 and 900 psi.

5. A method of producing a transgenic flax plant comprising:

preculturing a flax hypocotyl comprising epidermal tissue for about 4 days on a regeneration induction medium;

bombarding the precultured flax hypocotyl with a microprojectile at an acceleration pressure of between 650 and 900 psi, wherein the microprojectile comprises a nucleic acid and the bombardment is performed in a vacuum chamber under at least 26 inches Hg chamber vacuum, thereby producing a transformed flax hypocotyl comprising transformed flax cells that comprise the nucleic acid; and regenerating a transgenic flax plant from the transformed flax hypocotyl.

* * * * *

UNITED STATES PATENT AND TRADEMARK OFFICE
CERTIFICATE OF CORRECTION

PATENT NO. : 5,973,227
DATED : October 26, 1999
INVENTOR(S) : McHughen et al.

It is certified that error appears in the above-identified patent and that said Letters Patent is hereby corrected as shown below:

Column 2,
Lines 6 and 30, in all three occurrences, the colon ":" should be a semi-colon -- ; --.

Column 5,
Line 15, "CaCi$_2$-sapermidine" should be -- CaCl$_2$-spermidine --
Line 22, "70 L" should be -- 70 μL --.

Column 8,
Line 52, in footnote 4 to Table 2, "#GUS" should be -- #GUS$^-$ --.

Signed and Sealed this

Twenty-first Day of September, 2004

JON W. DUDAS
*Director of the United States Patent and Trademark Office*